United States Patent [19]

Fujino et al.

[11] 4,358,440
[45] Nov. 9, 1982

[54] POLYPEPTIDE AND ITS PRODUCTION AND USE

[75] Inventors: Masahiko Fujino, Takarazuka; Mitsuhiro Wakimasu, Suita; Chieko Kitada, Sakai, all of Japan

[73] Assignee: Takeda Chemical Industries, Ltd., Osaka, Japan

[21] Appl. No.: 226,600

[22] Filed: Jan. 21, 1981

[30] Foreign Application Priority Data

Jan. 2, 1980 [JP] Japan ................................. 55-11868

[51] Int. Cl.³ ..................... A61K 37/00; C07C 103/52
[52] U.S. Cl. .............................. 424/177; 260/112.5 E
[58] Field of Search .................. 260/112.5 E; 424/177

[56] References Cited

U.S. PATENT DOCUMENTS 4,038,222 7/1977 Li ................................. 260/112.5 E

*Primary Examiner*—Delbert R. Phillips
*Attorney, Agent, or Firm*—Hubbell, Cohen, Stiefel & Gross

[57] ABSTRACT

Novel polypeptide of the formula:

H-Tyr-Gly-Gly-Phe-Met-Lys-Pro-Tyr-Thr-Lys-Gln-Ser-His-Lys-Pro-Leu-Ile-Thr-Leu-Leu-Lys-His-Ile-Thr-Leu-Lys-Asn-Glu-Gln-OH is useful as an analgesic agent. Methods of its preparation are also disclosed.

2 Claims, No Drawings

POLYPEPTIDE AND ITS PRODUCTION AND USE

BACKGROUND OF THE INVENTION

1. Field of the Invention

The present invention relates to a novel polypeptide and to a process for producing the same.

2. Description of the Prior Art

Among the endorphins which are brain peptides in mammals, beta-endorphin is a particularly important physiological peptide, exhibiting a variety of the physiologic activities, such as analgesic action, growth hormone secretion stimulating action, prolactin secretion stimulating action and neurotropic action. When administered by the intracerebral route, it exerts an analgesic effect in rats and mice [Science, Vol. 194, p. 630 (1976); Proceedings of the National Academy of Science of the United States of America, Vol. 73, No. 8, p. 2895 (1976), etc.].

Salmon endorphin, scientifically known as *Oncorhynchus keta,* has been isolated, and its chemical structure was recently elucidated by Kawauchi et al. The chemical structure has been identified as Acetyl-Tyr-Gly-Gly-Phe-Met-Lys-Pro-Tyr-Thr-Lys-Gln-Ser-His-Lys-Pro-Leu-Ile-Thr-Leu-Leu-Lys-His-Ile-Thr-Leu-Lys-Asn-Glu-Gln-OH. See Biochemical and Biophysical Research Communications, Vol. 88, No. 4, pages 1249–1254 (1979).

SUMMARY OF THE INVENTION

The present inventors have found that despite the fact that the salmon endorphin in no way binds to the opiate receptor and therefore cannot be expected to exhibit an analgesic action, the following novel peptide, which is devoid of the acetyl group, possesses excellent analgesic action. The novel peptide is of the formula:

H-Tyr-Gly-Gly-Phe-Met-Lys-Pro-Tyr-Thr-Lys-
Gln-Ser-His-Lys-Pro-Leu-Ile-Thr-Leu-Leu-Lys-
His-Ile-Thr-Leu-Lys-Asn-Glu-Gln-OH. (I)

The present invention relates to:

(1) said novel compound (I), inclusive of its salts;

(2) a process for producing compound (I), which comprises subjecting a compound (II) of the general formula:

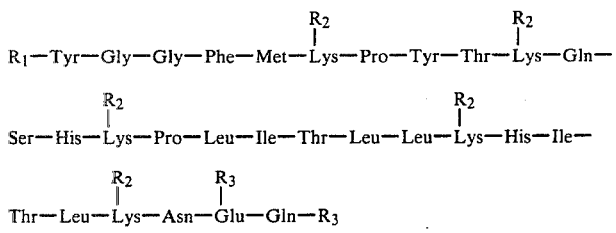

wherein $R_1$, $R_2$ and $R_3$ are each protective groups, to a reaction so as to remove its protective groups;

(3) a compound (III) of the general formula;

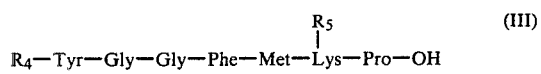

wherein $R_4$ and $R_5$ are each hydrogen or a protective group; and (4) an analgesic composition which comprises an analgesically effective amount of a compound of the formula (I), i.e., H-Tyr-Gly-Gly-Phe-Met-Lys-Pro-Tyr-Thr-Lys-Gln-Ser-His-Lys-Pro-Leu-Ile-Thr-Leu-Leu-Lys-His-Ile-Thr-Leu-Lys-Asn-Glu-Gln-OH, or a salt thereof, together with a pharmaceutically acceptable carrier.

DESCRIPTION OF THE PREFERRED EMBODIMENTS

In this specification, amino acids and peptides are designated either by the abbreviations commonly used in the art or by those adopted by the Committee on Chemical Nomenclature of the IUPAC-IUB. For example, amino acids are represented by use of the three-letter abbreviations and all denote the L-forms.

With respect to amino acids or peptides, use is made of the following abbreviations:
Asn: asparagine
His: histidine
Ile: isoleucine
Gln: glutamine
Glu: glutamic acid
Gly: glycine
Leu: leucine
Lys: lysine
Met: methionine
Phe: phenylalanine
Pro: proline
Ser: serine
Thr: threonine
Tyr: tyrosine The other abbreviations in common use and used herein are as follows:
Boc: t-butoxycarbonyl
Z: benzyloxycarbonyl
—OBu$^t$: t-butyl ester
DCC: N,N'-dicyclohexylcarbodiimide
DCU: N,N'-dicyclohexyl urea
HONB: N-hydroxy-5-norbornene-2,3-dicarboximide
—ONB: HONB ester
—SDP: 4,6-dimethyl-2-mercaptopyrimidine.thioester
TEA: triethylamine
DCHA: dicyclohexylamine
TFA: trifluoroacetic acid
AcOEt: ethyl acetate
DMF: dimethylformamide
THF: tetrahydrofurane

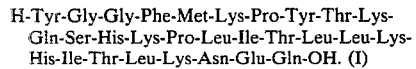

HOBt: 1-hydroxybenzotriazole
MeOH: methanol
EtOH: ethanol
BuOH: butanol

The protective groups represented by $R_1$, $R_2$, $R_4$ and $R_5$ in the above general formulas include the protective groups for the amino group employed in the peptide condensation reaction, such as t-butoxycarbonyl, benzyloxycarbonyl, t-amyloxycarbonyl, isobornyloxycarbonyl, adamantyloxycarbonyl, o-nitrophenylthio, diphenylphosphinothioyl, dimethylphosphinothioyl, chloro- or nitro- substituted benzyloxycarbonyl, and the like. The protective groups represented by $R_1$, $R_2$, $R_4$ and $R_5$ may each be the same or different. The protective group represented by $R_3$ includes the protective groups for the carboxyl group employed in the peptide condensation reaction, such as methyl, ethyl, t-butyl, benzyl, chloro- or nitro- substituted benzyl, sec-butyl, cyclopentyl, cyclohexyl, diphenylmethyl (as an ester form), etc.

Production of compound (I) of the present invention is carried out by condensing a segmentary amino acid or its peptide capable of constituting a part of the polypeptide of compound (I) with a compound capable of constituting the remaining part thereof by means of a peptide synthesis procedure. Said peptide synthesis procedure may be in accordance with any of the known methods as described in M. Bodanszky and M. A. Ondetti: Peptide Synthesis, Interscience Publishers, New York, 1966; F. M. Finn and K. Hofmann: The Proteins, Vol. 2, edited by H. Nenrath, R. L. Hill, Academic Press Inc., New York; Nobuo Izumiya, et al: Peptide Gosei (Peptide Synthesis), Maruzen Inc., Japan, 1975, and the like, such as the azide method, chloride method, mixed acid anhydride method, DCC method, active ester method, the method involving the use of Woodward's reagent K, carbodiimidazole method, oxidation-reduction method, DCC/HONB method, etc. In certain circumstances, the NCA (N-carboxyanhydride) method (the method involving the use of an intramolecular cyclic carbonyl compound corresponding to the amino acid without use of a protective group) may be applied.

Prior to the condensation reaction, the carbonyl and/or amino group of the starting material which will not be pertinent to the reaction may be protected, or the carboxyl and/or amino group of the starting material which is pertinent to the reaction may be activated.

The protective groups for the starting material include the protective groups mentioned hereinabove. The carboxyl group of the starting material can also be protected in the form of a metal salt (e.g., sodium salt, potassium salt, etc.), t-alkylamine salt (e.g., triethylamine salt, N-methylmorpholine salt, etc.) or ester (e.g., methyl ester, ethyl ester, benzyl ester, p-nitrobenzyl ester, t-butyl ester, t-amyl ester, etc.). As examples of the protective group for the amino group of the starting material, there may be mentioned benzyloxycarbonyl, t-butoxycarbonyl, isobornyl oxycarbonyl, etc., while examples of the protective group for the imino group of hisidine include benzyl, tosyl, 2,4-dinitrophenyl, t-butyloxycarbonyl, carbobenzoxy, and the like. The protective group for the hydroxyl group of tyrosine may be exemplified by ethers of benzyl, t-butyl, etc.

As examples of the activated form of the carboxyl group in the starting material, there may be mentioned the corresponding acid anhydride, azide and active ester [i.e., esters with alcohols (e.g., pentachlorophenol, 2,4,5-trichlorophenol 2,4-dinitrophenol, cyanomethyl alcohol, p-nitrophenol, N-hydroxy5-norbornene-2,3-dicarboximide, N-hydroxysuccineimide, N-hydroxyphthalmimide and N-hydroxybenzotriazole)]. As an example of the activated form of the amino group in the starting material, there may be mentioned the corresponding phosphoric acid amide.

Assuming that the starting materials are A and B, the above combinations of the carboxyl and amino groups in A and B are shown in the following table.

| Combination example | Starting materials | | | |
|---|---|---|---|---|
| | A | | B | |
| | COOH | NH₂ | COOH | NH₂ |
| 1* | Free | Protected | Protected | Free |
| 2 | Activated | Protected | Free | Free |
| 3 | Free | Protected | Protected | Activated |

Remarks: In the case of 1*, a dehydrating agent (e.g., a carbodiimide reagent such as dicyclohexylcarbodiimide) is desirably present in the reaction system.

The reaction can be conducted in the presence of a solvent. The solvent is desirably selected from among the solvents hitherto known to be suited for use in the peptide condensation reaction. Thus, for example, there may be mentioned anhydrous or aqueous dimethylformamide, dimethylsulfoxide, pyridine, chloroform, dioxane, dichloromethane and tetrahydrofuran, as well as suitable mixtures thereof.

The reaction temperature is desirably selected from the range hitherto known to be operable in the peptide bond forming reaction and normally is from about $-20°$ C. to about 30° C. The precursor compounds (protected peptides) for the compounds of this invention can be easily produced as well by the solid-phase synthesis procedure.

Compound (II) thus obtained is subjected to a deprotecting reaction. While the deprotecting reaction depends upon the type of protective groups involved, it is preferred for commercial purposes that this reaction is such that it will remove all the protective groups in a single step without affecting the peptide bonds. Therefore, the protective groups are desirably chosen in consideration of this possibility.

Conditions for such deprotecting reaction include, for example, catalytic reduction using a catalyst such as palladium black, palladium-on-carbon, platinum, etc. and acid treatment with trifluoroacetic acid, dilute hydrochloric acid, methanesulfonic acid, etc., and there may be further mentioned reduction with sodium metal in liquid ammonia and acid treatment with formic acid, trifluoromethanesulfonic acid, hydrogen fluoride, etc. These reactions are generally conducted at suitable temperatures of from about $-20°$ C. to about 40° C., and in the case of acid decomposition, addition of a cation acceptor such as water, anisole, phenol and/or thionanisole may be desirable.

After conclusion of the reaction, compound (I) produced in this way is collected by the isolation procedure for peptides, such as extraction, distribution, reprecipitation, recrystallization and column chromatography.

Compound (III) can also be produced by the same procedures as described above.

Compound (I) can be obtained in the form of a salt with an organic or inorganic acid, etc., by conventional procedures. Preferred examples of such salts generally include the acetate, citrate, tartrate, hydrochloride, sulfate and phosphate.

Compound (I) exhibits a binding strength with the opiate receptor (brain) which, without the addition of sodium, is about 2.71 times greater, and with the addition of sodium, is about 3.05 times greater than that of the human beta-endorphin.

This binding activity is about 4.6 times greater, and about 3.74 times greater, respectively, than that of morphine. Therefore, this peptide (I) is an analgesic agent that is far superior to beta-endorphin. It can be chemically synthesized more easily than beta-endorphin. Hence, this peptide (I) is believed to be of great importance as a drug.

The above experiment was carried out by the procedure as described in The Journal of Biological Chemistry, Vol. 254, No. 8, p. 2610 (1979).

In addition, compound (I) is of very low toxicity. Compound (I) can be applied to mammals (e.g., mouse, rat, man, etc.) as an analgesic agent, neurotropic agent, etc. Compound (I) and its pharmacologically acceptable acid addition salts are of value as an analgesic agent against the intense pain accompanied with the late stage of a cancer disease or encountered after an operation. Compound (I), when administered in the course of a delivery, permits a substantially painless delivery to be realized with safety.

As examples of pharmaceutically acceptable carriers there may be mentioned sugars such as glucose, fructose, mannitol, sorbitol and lactose.

The dosage of compound (I) to warm-blooded animals varies with the symptom and type of hosts to be administered, and is generally in the range of about 0.2 to 200 μg/kg daily, most preferably in the range of about 10 to 80 μg/kg daily. Compound (I) is desirably administered parenterally. Particularly effective is the method of infusing it into the lumbar vertebra as an injection. In addition, compound (I) finds application as a growth hormone release stimulating agent or prolactin release stimulating agent, and, in such instances, intravenous administration as an injection is most preferred.

Preparation of injections can be effected, for example, by dissolving 2 mg of compound (I) or its salt [2 mg in terms of compound (I)] in 2 ml of physiological saline, filling an ampoule with this solution, and after closing the ampoule, heating at 110° C. for 30 minutes to effect sterilization, or by dissolving 1 mg of the compound or its salt [1 mg in terms of compound (I)] together with 10 mg of mannitol or sorbitol in 1 ml of sterilized distilled water, filling an ampoule with the solution, freeze-drying it, then closing the ampoule. The freeze-dried preparation is used as an injection by dissolving in physiological saline solution.

Compound (III) of the present invention can be used as an intermediate for peptide synthesis. Compound (III) can be utilized, for example, as an intermediate for the production of compound (I) of the present invention.

The examples given below illustrate the present invention more specifically.

In the thin-layer chromatography utilized in the examples, Silica gel 60F-254 (produced by E. Merck A. G., West Germany) or Avicel (produced by Funakoshi Pharmaceutical Co., Japan) was employed as a carrier, using the following solvent systems:

$Rf^1$; chloroform:methanol:acetic acid=9:1:0.5
$Rf^2$; ethyl acetate:pyridine:acetic acid:water=60:20:6:11
$Rf^3$; n-butanol:acetic acid:water=4:1:1
$Rf^4$; n-butanol:pyridine:acetic acid:water=30:20:6:24
$Rf^5$; ethyl acetate:n-butanol:acetic acid:water=1:1:1:1
$Rf^6$; chloroform:methanol:water=7:3:0.5

Shown in Table 1 is the mode of production of the compound (I) in the following examples.

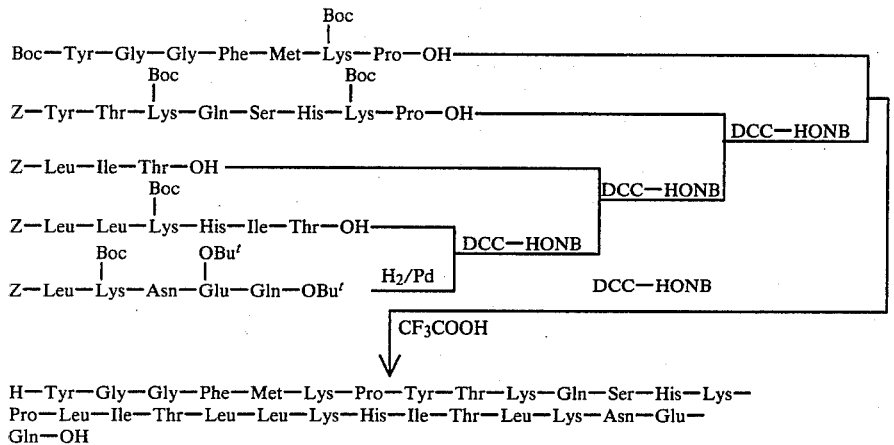

H—Tyr—Gly—Gly—Phe—Met—Lys—Pro—Tyr—Thr—Lys—Gln—Ser—His—Lys—Pro—Leu—Ile—Thr—Leu—Leu—Lys—His—Ile—Thr—Leu—Lys—Asn—Glu—Gln—OH

More specifically, successive Examples 1–4 relate to the production of Z-Leu-Lys(Boc)-Asn-Glu(OBu$^t$)-Gln-OBu$^t$.

Successive Examples 5–9 relate to the production of Z-Leu-Leu-Lys(Boc)-His-Ile-Thr-OH.

With respect to the production of the compound Z-Tyr-Thr-Lys(Boc)-Gln-Ser-His-Lys(Boc)-Pro-OH, successive Examples 11–12 relate to the production of the precursor Z-His-Lys(Boc)-Pro-OH; successive Examples 13–17 relate to the production of the precursor Z-Tyr-Thr-Lys(Boc)-Gln-Ser-NHNH$_2$; and Example 18 relates to the reaction of the foregoing precursors to form said compound.

With respect to the production of the compound Boc-Tyr-Gly-Gly-Phe-Met-Lys(Boc)-Pro-OH, Example 19 relates to the production of the precursor Z-Lys(Boc)-Pro-OBu$^t$; successive Examples 20–21 relate to the production of the precursor Boc-Phe-Met(O)-OH.DCHA; successive Examples 22–23 relate to the production of the precursor Z-Tyr-Gly-Gly-OH; and successive Examples 24–28 relate to the utilization of said precursors to form said compound. It is to be noted that said compound that is, the compound of Example 28, is a species of the compounds embraced by general formula (III), i.e., R$_4$-Tyr-Gly-Gly-Phe-Met-Lys(R$_5$)-Pro-OH.

Successive Examples 29–31 relate to the production of the compound Z-Tyr-Thr-Lys(Boc)-Gln-Ser-His-Lys(Boc)-Pro-Ile-Thr-Leu-Leu-Lys(Boc)-His-Ile-Thr-Leu-Lys(Boc)-Asn-Glu(OBu$^t$)-Gln-OBu$^t$.

Example 32 entails the use of the compound of Example 28 and the compound of Example 31 to produce the compound Boc-Tyr-Gly-Gly-Phe-Met-Thr-Lys(Boc)-Pro-Tyr-Thr-Lys(Boc)-Gln-Ser-His-Lys(Boc)-Pro-Leu-Ile-Thr-Leu-Leu-Lys(Boc)-His-Ile-Thr-Leu-Lys(Boc)-Asn-Glu(OBu$^t$)-Gln-OBu$^t$. Note that this latter compound is a species of the compounds embraced by general formula II, i.e., R$_1$-Tyr-Gly-Gly-Phe-Met-Lys(R$_2$)-Pro-Tyr-Thr-Lys(R$_2$)-Gln-Ser-His-Lys(R$_2$)-Pro-Leu-Ile-Thr-Leu-Leu-Lys(R$_2$)-His-Ile-Thr-Leu-Lys(R$_2$)-Asn-Glu(R$_3$)-Gln-R$_3$.

Example 33 relates to the production of the compound of formula (I) by removal of the protective groups from the compound of Example 32.

EXAMPLE 1

Production of Z-Glu(OBu$^t$)-Gln-OBu$^t$

In 300 ml of AcOEt there were suspended 25.9 g of Z-Glu-(OBu$^t$)-OH·DCHA, and 110 ml of 0.5 N sulfuric acid were added to the suspension, and the whole was shaken, followed by washing with water and subsequently drying over anhydrous sodium sulfate. After distilling off the solvent, the residue was dissolved in 200 ml of THF, and 9.9 g of HONB and 11.4 g of DCC were added to the solution under cooling with ice. The mixture was stirred for 15 hours, and the precipitated DCU was filtered out. Separately 16.8 g of Z-Gln-OBu$^t$ were dissolved in 250 ml of MeOH to conduct catalytic reduction for 4 hours with Pd black used as the catalyst. After filtering out the catalyst and distilling off the solvent, 100 ml of THF was added, and the active ester as previously prepared was added to the mixture and the mixture was stirred at room temperature for 15 hours. The solvent was distilled off, and the residue was dissolved in 300 ml of AcOEt, washed with aqueous sodium hydrogencarbonate and aqueous citric acid, the dried over anhydrous sodium sulfate. The solvent was distilled off and the residue was treated with diethyl ether, and crystals were recovered by filtration to give a yield of 23.5 g (90.1%); m.p. 117°–118° C.; $[\alpha]_D^{23} - 17.2°$ (c = 1.00, DMF); Rf$^1$ = 0.66.

Elemental analysis, for C$_{26}$H$_{39}$O$_8$N$_3$: Calcd.: C, 59.87; H, 7.54; N, 8.06; Found: C, 59.80; H, 7.47; N, 8.24

EXAMPLE 2

Production of Z-Asn-Glu(OBu$^t$)-Gln-OBu$^t$ 13.7 g of Z-Glu(OBu$^t$)-Gln-OBu$^t$ were catalytically reduced in 200 ml of MeOH, and then the solvent was distilled off, followed by dissolving the residue in 100 ml of DMF. 6.0 g of Z-Asn-OH and 5.2 g of HONB were added to the solution and, after cooling with ice, 6.0 g of DCC was added to the mixture, followed by stirring for 15 hours. The resulting precipitates, DCU, were removed by filtration. The remaining solution was subjected to distillation to remove the solvent. To the residue were then added 150 ml of AcOEt. The resulting gel was collected by filtration, which was crystallized from acetonitrile, and crystals were recovered by filtration to give a yield of 16.6 g (97.9%): m.p. 185°–187° C.; $[\alpha]_D^{23} - 21.4°$ (c = 1.19, DMF); Rf$^1$ = 0.42.

Elemental analysis, for C$_{30}$H$_{45}$O$_{10}$N$_5$·½H$_2$O: Calcd.: C, 55.88; H, 7.19; N, 10.86; Found: C, 56.05; H, 7.14; N, 11.08

EXAMPLE 3

Production of Z-Lys(Boc)-Asn-Glu(OBu$^t$)-Gln-OBu$^t$ 8.26 g of Z-Asn-Glu(OBu$^t$)-Gln-OBu$^t$ were catalytically reduced in 300 ml of DMF, and then Z-Lys(Boc)-ONB [prepared using 7.70 g of Z-Lys(Boc)-OH·DCHA] were added. The mixture was stirred at room temperature for 15 hours. After distilling off the solvent, 150 ml of AcOEt were added to the residue. The resulting gel was collected by filtration, and washed with EtOH. Yield 8.90 g (79.2%); m.p. 213°–214° C. (decomp.); $[\alpha]_D^{23} - 20.5°$ (c = 0.99, DMF); Rf$^1$ = 0.50

Elemental analysis, for C$_{41}$H$_{65}$O$_{13}$N$_7$: Calcd.: C, 56.99; H, 7.58; N. 11.35; Found: C, 56.80; H, 7.54; N, 11.49

EXAMPLE 4

Production of Z-Leu-Lys(Boc)-Asn-Glu(OBu$^t$)-Gln-OBu$^t$ 8.0 g of Z-Lys(Boc)-Asn-Glu(OBu$^t$)-Gln-OBu$^t$ were catalytically reduced in 200 ml of DMF, and then Z-Leu-ONB (prepared using 4.2 g of Z-Leu-OH·DCHA) was added, followed by stirring at room temperature for 15 hours. After distilling off the solvent, the residue was treated with 100 ml of water. The resulting gel was collected by filtration and washed with aqueous acetonitrile. Yield 7.35 g (81.2%); m.p. 214°–216° C. (decomp.); $[\alpha]_D^{21.5} - 22.4°$ (c = 0.98, DMF); Rf$^1$ 0.53.

Elemental analysis, for C$_{47}$H$_{76}$O$_{14}$N$_8$: Calcd.: C, 57.77; H, 7.84; N, 11.47; Found: C, 57.69; H, 7.93; N, 11.42

EXAMPLE 5

Production of Z-Ile-Thr-OH

In 500 ml of a mixed solvent of dioxane and ethyl acetate (1:1) were dissolved 24.3 g of Z-Ile-OH and 19.8 g of HONB. The solution was cooled with ice, followed by adding 20.8 g of DCC. The mixture was stirred for two hours. The precipitating DCU was removed by filtration, then the solvent was removed by distillation. The residue was crystallized from petroleum benzine. The crystals were recovered by filtration and dissolved in 200 ml of DMF. Separately 18 g of Thr and 12.8 ml of TEA were dissolved in a mixed solvent consisting of 200 ml of water and 50 ml of DMF. The solution was cooled with ice, and then the previously prepared DMF solution of activated ester was added. The mixture was stirred for one hour, and further stirred for 14 hours at a room temperature. Insolubles were removed by filtration, then the solvent was evaporated off. The residue was dissolved in 300 ml of 5% aqueous solution of sodium hydrogen-carbonate, and the solution was washed with diethyl ether. The aqueous layer was separated and acidified with 1N-hydrochloric acid, followed by two extractions, each with a 200 ml portion of AcOEt. The extracts were combined and washed with water, followed by drying over anhydrous sodium sulfate. The solvent was then evaporated off. To the residue was then added AcOEt-diethyl ether, and the resulting crystals were recovered by filtration. Yield 24.4 g (72.8%); m.p. 160°–162° C.; $[\alpha]_D^{24} - 10.3°$ (c = 0.57, MeOH); Rf$^1$ = 0.36

Elemental analysis, for C$_{18}$H$_{26}$O$_6$N$_2$: Calcd.: C, 59.00; H, 7.15; N, 7.66; Found: C, 58.82; H, 7.19; N, 7.59

EXAMPLE 6

Production of Boc-His(Tos)-Ile-Thr-OH 11.0 g of Z-Ile-Thr-OH were catalytically reduced in 350 ml of aqueous methanol, then the solvent was distilled off, and the residue was dissolved in 300 ml of aqueous DMF. 4.2 ml of TEA and Boc-His(Tos)-ONB [prepared using 21.3 g of Boc-His(Tos)-OH·DCHA]

were added to the solution, followed by stirring for 15 hours. The mixture was as described in Example 5, and reprecipitated twice from diethyl ether-petroleum benzine. Yield 8.1 g (43.3%); m.p. 114°–118° C.; $[\alpha]_D^{24} - 5.1°$ (c=0.57, MeOH); $Rf^1 = 0.47$.

Elemental analysis, for $C_{28}H_{41}O_9N_5S.\frac{1}{2}AcOEt$: Calcd.: C, 53.96; H, 6.79; N, 10.49; S, 4.80; Found: C, 54.68; H, 6.78; N, 10.47; S, 4.97

EXAMPLE 7

Production of Z-Lys(Boc)-His-Ile-Thr-OH

In 100 ml of THF were dissolved 7.25 g of Boc-His-(Tos)-Ile-Thr-OH, and 2.7 g of HOBt were added, followed by stirring at room temperature for 60 minutes and subsequently distilling off the solvent. The residue was dissolved in 40 ml of TFA, and the solution was shaken at room temperature for 30 minutes. The solvent was distilled off, and the residue was treated with diethyl ether. The resulting powder was recovered by filtration and dried. The product was dissolved in 200 ml of DMF, and 2.8 ml of TEA and Z-Lys(Boc)-ONB [prepared using 6.74 g of Z-Lys(Boc)-OH.DCHA] were added, following by stirring at room temperature for 20 hours. The solvent was distilled off, and the residue was dissolved in a small amount of water and washed with diethyl ether followed by further addition of water. The resulting gel was collected by filtration, which was reprecipitated from AcOEt-DMF-diethyl ether and purified by a column of Cephadex LH-20. Yield 3.4 g (46.6%); m.p. 192°–194° C. (decomp.); $[\alpha]_D^{27} - 24.6°$ (c=0.46, MeOH); $Rf^2 = 0.42$.

Elemental analysis, for $C_{35}H_{53}O_{10}N_7.H_2O$: Calcd.: C, 56.06; H, 7.39; N, 13.07; Found: C, 56.12; H, 7.34; N, 13.18

EXAMPLE 8

Production of Z-Leu-Lys(Boc)-His-Ile-Thr-OH 4.0 g of Z-Lys(Boc)-His-Ile-Thr-OH were catalytically reduced in 200 ml of 70% aqueous methanol, the solvent was distilled off, and the residue was dissolved in 100 ml of DMF. 0.77 ml of TEA and Z-Leu-ONB [prepared using 2.03 g of Z-Leu-OH] were added to the solution, and the mixture was stirred at room temperature for 16 hours. The solvent was distilled off, and the residue, after adding 1 ml of acetic acid, was treated with acetonitrile. The resulting powder was recovered by filtration and washed with EtOH-diethyl ether. Yield 3.0 g (65.0%); m.p. 204°–207° C. (decomp.); $[\alpha]_D^{27} - 30.0°$ (c=0.40, MeOH); $Rf^2 = 0.50$.

Elemental analysis, for $C_{41}H_{64}O_{11}N_8.3/2H_2O$: Calcd.: C, 56.47; H, 7.74; N, 12.85; Found: C, 56.32; H, 7.53; N, 12.85

EXAMPLE 9

Production of Z-Leu-Leu-Lys(Boc)-His-Ile-Thr-OH 3.0 g of Z-Leu-Lys(Bos)-His-Ile-Thr-OH were catalytically reduced in 150 ml of 70% aqueous methanol, the solvent was distilled off, and the residue was dissolved in 100 ml of DMF. 0.5 ml of TEA and Z-Leu-ONB [prepared using 1.13 g of Z-Leu-OH] were added to the solution, and the mixture was stirred at room temperature for 16 hours. The solvent was distilled off, and the residue was treated with 0.5 ml of acetic acid and a small amount of acetonitrile. The resulting powder was recovered by filtration and the powder was crystallized from methanol. Yield 2.55 g (75.0%); m.p. 227°–228° C.; $[\alpha]_D^{27} - 39.7°$ (c=0.35, MeOH); $Rf^2 = 0.60$.

Elemental analysis, for $C_{47}H_{75}O_{12}N_9.H_2O$: Calcd.: C, 57.83; H, 7.95; N, 12.92; Found: C, 58.07; H, 7.93; N, 13.07

EXAMPLE 10

Production of Z-Leu-Ile-Thr-OH 8.8 g of Z-Ile-Thr-OH were catalytically reduced in 300 ml of 70% aqueous methanol, the solvent wad distilled off, and the residue was dissolved in 250 ml of 70% aqueous DMF. 3.36 ml of TEA and Z-Leu-ONB [prepared using 5.3 g of Z-Leu-OH] were added to the solution, and the mixture was stirred for 16 hours. After distilling off the solvent, the residue was purified in the manner of Example 5 and crystallized from AcOEt-petroleum ether. Recrystallization from EtOH-petroleum ether gave 8.0 g of the desired product. (70.0%); m.p. 146°–148° C.; $[\alpha]_D^{24} - 36.0°$ (c=0.18, MeOH); $Rf^1 = 0.45$.

Elemental analysis, for $C_{24}H_{37}O_7N_3$: Calcd.: C, 60.11; H, 7.78; N, 8.76; Found: C, 59.76; H, 7.59; N, 8.59

EXAMPLE 11

Production of Z-Lys(Boc)-Pro-OH

In 50 ml of DMF were dissolved 2.53 g of Pro, and 3.08 ml of TEA were added to the solution after cooling with ice. A solution of Z-Lys(Boc)-ONB [prepared using 7.61 g of Z-Lys(Boc)-OH] in 50 ml of DMF was added to the mixture, followed by stirring at room temperature for 12 hours. To the reaction mixture was added 5 ml of acetic acid. Then the solvent was distilled off. The residue was dissolved in AcOEt. The solution was washed with 0.1 N hydrochloric acid and with water, which was dried over anhydrous sodium sulfate, followed by distilling off the solvent. The resultant was chromatographed on a column (7.0×15.0 cm) of silica gel. Elution with 5% MeOH/CHCl$_3$ was carried out to collect the objective fractions. Yield 8.45 g (88.5%), an oily substance; $Rf^1 = 0.52$.

EXAMPLE 12

Production of Z-His-Lys(Boc)-Pro-OH 8.45 g of Z-Lys(Boc)-Pro-OH were catalytically reduced in 200 ml of MeOH, the solvent was distilled off, and the residue was dissolved in 50 ml of DMF. To the solution were added, under ice-cooling, 2.48 ml of TEA and a solution of Z-His-N$_3$ [prepared using 5.91 g of Z-His-NHNH$_2$] in AcOEt, followed by stirring at 4° C. for 48 hours. After adding 17.7 ml of 1 N hydrochloric acid to the reaction solution to neutralize, the solvent was distilled off. To the residue was added diethyl ether, and the resulting powder was recovered by filtration. The product was placed on the column (7.0×20.0 cm) of silica gel and eluted with a solvent of AcOEt: pyridine: acetic acid: water (60:20:6:10), then the objective fractions were collected and treated with diethyl ether, whereby powdery product was obtained. Yield 6.2 g (56.9%), m.p. 86°–90° C. (decomp.); $[\alpha]_D^{22} - 25.5°$ (c=0.7, DMF); $Rf^2 = 0.26$.

Elemental analysis, for $C_{30}H_{42}O_8N_6.H_2O$: Calcd.: C, 56.95; H, 7.01; N, 13.28; Found: C, 57.02; H, 7.03; N, 12.15

EXAMPLE 13

Production of Z-Gln-Ser-OMe

In 100 ml of DMF were suspended 6.22 g of H-Ser-OMe.HCl, and the suspension was cooled with ice and 5.60 ml of TEA were added. A solution of Z-Gln-ONB [prepared using 11.2 g of Z-Gln-OH] in 30 ml of DMF was added to the solution, followed by stirring at room temperature for 12 hours. The insolubles were removed by filtration, and the filtrate was subjected to distilation to remove the solvent. To the residue was added diethyl ether, and the resulting precipitates were recovered by filtration. The product was recrystallized from aqueous methanol. Yield 12.5 g (82.0%); m.p. 173°–174° C.; $[\alpha]_D^{22} +1.8$ (c=0.7, DMF), $Rf^1 = 0.20$.

Elemental analysis, for $C_{17}H_{23}O_7N_3$: Calcd.: C, 53.53; H, 6.08; N, 11.02; Found: C, 54.11; H, 6.71; N, 11.78

EXAMPLE 14

Production of Z-Lys(Boc)-Gln-Ser-OMe

In 150 ml of MeOH were dissolved 7.63 g of Z-Gln-Ser-OMe and catalytic reduction was carried out in the presence of 3.80 g of p-toluenesulfonic acid. The solvent was distilled off, and the residue was dissolved in 100 ml of DMF. The solution was cooled with ice, and 2.80 ml of TEA and a solution of Z-Lys(Boc)-ONB [prepared using 7.60 g of Z-Lys(Boc)-OH] in 30 ml of DMF were added, followed by stirring at 0° C. for 4 hours and then at room temperature for 12 hours. The insolubles were removed by filtration, and the filtrate was subjected to distillation to remove the solvent, followed by addition of water. The resulting precipitates were recovered by filtration, then recrystallized from AcOEt. Yield 9.20 g (75.4%); m.p. 176°–177° C.; $[\alpha]_D^{22} -8.4°$ (c=0.6, DMF); $Rf^1=0.22$.

Elemental analysis, for $C_{28}H_{43}O_{10}N_5 \cdot \frac{1}{2}H_2O$: Calcd.: C, 54.36; H, 7.17; N, 11.32; Found: C, 54.36; H, 7.15; N, 11.54

EXAMPLE 15

Production of Z-Thr-Lys(Boc)-Gln-Ser-OMe 4.27 g of Z-Lys(Boc)-Gln-Ser-OMe were catalytically reduced in 150 ml of MeOH, the solvent was distilled off, and the residue was dissolved in 20 ml of DMF. To the solution were added, under ice-cooling, 3.05 g of Z-Thr-ONB, and the mixture was stirred at room temperature for 12 hours. The insolubles were filtered out, and the filtrate was subjected to distillation to remove the solvent. To the resulting residue was added diethyl ether, and the resulting precipitates were recovered by filtration. The product was recrystallized twice from acetonitrile. Yield 4.51 g (90.6%); m.p. 201°–202° C. (decomp.); $[\alpha]_D^{22} -9.3°$ (c=0.5, DMF); $Rf^1 = 0.12$.

Elemental analysis, for $C_{32}H_{50}O_{12}N_6$: Calcd.: C, 54.07; H, 7.09; N, 11.82; Found: C, 53.80; H, 7.26; N, 11.84

EXAMPLE 16

Production of Z-Tyr-Thr-Lys(Boc)-Gln-Ser-OMe 4.26 g of Z-Thr-Lys(Boc)-Gln-Ser-OMe were catalytically reduced in 150 ml of MeOH, the solvent was distilled off and the residue was dissolved in 20 ml of DMF. 3.43 g of Z-Tyr-ONB were added to the solution and the mixture was stirred at room temperature for 12 hours. The insolubles were removed by filtration, and the filtrate was subjected to distillation to remove the solvent. To the residue was added diethyl ether, and the resulting precipitates were recovered by filtration. The product was recrystallized from acetonitrile. Yield 5.0 g (95.4%); m.p. 181°–183° C. (decomp.); $[\alpha]_D^{22} -10.3°$ (c=0.5, DMF); $Rf^1=0.06$; $Rf^2=0.84$.

Elemental analysis, for $C_{41}H_{59}O_{14}N_7$: Calcd.: C, 56.35; H, 6.80; N, 11.22; Found: C, 56.21; H, 7.15; N, 11.00

EXAMPLE 17

Production of Z-Tyr-Thr-Lys(Boc)-Gln-Ser-NHNH$_2$

In 270 ml of MeOH were dissolved 3.93 g of Z-Tyr-Thr-Lys(Boc)-Gln-Ser-OMe, and 2.5 ml of $NH_2NH_2 \cdot H_2O$ was added to the solution, followed by allowing the mixture to stand at room temperature for 48 hours. The resulting crystals were recovered by filtration and recrystallized from MeOH. Yield 3.4 g (86.5%); m.p. 204°–205° C. (decomp.); $[\alpha]_D^{22} -9.0°$ (c=0.5, DMF); $Rf^2=0.36$.

Elemental analysis, for $C_{40}H_{59}O_{13}N_9$: Calcd.: C, 54.97; H, 6.80; N, 14.42; Found: C, 54.63; H, 6.98; N, 14.31

EXAMPLE 18

Production of Z-Tyr-Thr-Lys(Boc)-Gln-Ser-His-Lys(Boc)-Pro-OH 2.27 g of Z-His-Lys(Boc)-Pro-OH were catalytically reduced in 100 ml of MeOH, the solvent was distilled off, and the residue was dissolved in 20 ml of DMF, followed by adding 0.52 ml of TEA to neutralize. Separately, 3.23 g of Z-Tyr-Thr-Lys(Boc)-Gln-Ser-NHNH$_2$ were dissolved in 80 ml of DMF, and the solution was cooled at $-20°$ C. 1.6 ml of 9.2 N-HCl/dioxane was added to the solution, to which 0.6 ml of isoamyl nitrite was added dropwise under stirring at a temperature within the range of $-25°$ C. to $-18°$ C. While the mixture was stirred, two 0.2 ml portions of isoamyl nitrite were added at 10 and 20 minute intervals, respectively, and the mixture was stirred for 30 minutes in total. The reaction solution was cooled at $-60°$ C. and 2.4 ml of TEA were added to neutralize. A DMF solution of H-His-Lys(Boc)-Pro-OH was added to the solution, followed by stirring at $-20°$ C. for 1 hour and then at 4° C. for 48 hours. The solvent was distilled off and to the resulting residue was added diethyl ether. The resulting precipitates were recovered by filtration. Thr precipitates were dissolved in 50 ml of a 5% aqueous acetic acid while warming, and after cooling, the resulting precipitates were recovered by filtration. The product was recrystallized from hot acetonitrile and then from water. Yield 2.80 g (57.3%); m.p. 197°–198° C. (decomp.); $[\alpha]_D^{22} -21.2°$ (c=0.8, DMF); $Rf^2=0.12$.

Elemental analysis, for $C_{62}H_{91}O_{19}N_{13} \cdot 2H_2O$: Calcd.: C, 54.82; H, 7.05; N, 13.40; Found: C, 54.72; H, 7.03; N, 13.45

Amino acid analysis (5.7 N hydrochloric acid hydrolysis, 110° C., 24 hours): Lys 2.07(2), His 0.84(1), Thr 1.04(1), Ser 1.01(1), Glu 1.01(1), Pro 0.92(1), Tyr 1.01(1).

Average recovery rate was 95.3%.

EXAMPLE 19

Production of Z-Lys(Boc)-Pro-OBu$^t$ 1.53 g of Z-Pro-OBu$^t$ were catalytically reduced in 80 ml of MeOH, the solvent was distilled off, and the residue was dissolved in a mixed solution consisting of 50 ml of dioxane and 20 ml of AcOEt. 1.9 g of Z-Lys(Boc)-OH and 1.08 g of HONB were added to the solution, and the mixture was cooled with ice, followed by adding 1.14 g of DCC and stirring for 15 hours. The solvent was distilled off, and the residue was dissolved in 200 ml of AcOEt, washed with aqueous sodium hydrogencarbonate and 0.2 N-hydrochloric acid, further washed with water, and dried over anhydrous sodium sulfate. The solvent was distilled off, thereby resulting in an oily substance. Yield 2.7 g (100%); $Rf^1 = 0.75$.

EXAMPLE 20

Production of Boc-Phe-Met-OH

In 150 ml of water were dissolved under heating 16.4 g of Met and 9.24 g of sodium hydrogencarbonate, the solution was cooled to room temperature, and to the reaction solution were added 300 ml of a solution of Boc-Phe-ONB (prepared using 26.5 g of Boc-Phe-OH) in acetonitrile, followed by stirring for 40 hours. The reaction mixture was subjected to distillation to remove the solvent, and to the residue was added aqueous citric acid. The solution was extracted with 400 ml of AcOEt, washed with water and dried over anhydrous sodium sulfate. 18.1 g of DCHA were added to the extract, and the solvent was distilled off. To the resulting crude crystals was added diethyl ether, whereupon precipitates were formed. The precipitates were recovered by filtration and then suspended in 500 ml of AcOEt. To the suspension was added 320 ml of 0.25 N sulfuric acid, and the mixture was shaken sufficiently followed by washing with water and drying over anhydrous sodium sulfate. The solvent was removed by distillation, and petroleum benzine was added to the residue. The resulting crystals were recovered by filtration. Yield 31.0 g (78.2%); m.p. 134°–135° C.; $[\alpha]_D^{21} - 10.8°$ (c=0.99, DMF); $Rf^1 = 0.61$.

Elemental analysis, for $C_{19}H_{28}O_5N_2S$: Calcd.: C, 57.55; H, 7.12; N, 7.07; S, 8.09; Found: C, 57.50; H, 7.10; N, 7.00; S, 8.03

EXAMPLE 21

Production of Boc-Phe-Met(O)-OH.DCHA

In 500 ml of acetonitrile were dissolved 27.0 g of Boc-Phe-Met-OH, and 13 ml of a 30% aqueous hydrogen peroxide was added dropwise to the solution at room temperature, followed by stirring for 72 hours. 100 ml of water were added to the reaction solution, and 1 g of Pd black was added. After stirring for 4 hours, the catalyst was filtered out, and the solvent was distilled off. The residue was treated with a saturated aqueous solution of sodium chloride to extract with AcOEt, followed by drying over anhydrous sodium sulfate. To the product were added 12.3 g of DCHA, and the resulting crystals were recovered by filtration. The crystals were recrystallized from MeOH-diethyl ether. Yield 32.6 g (80.6%); m.p. 166°–169° C.; $[\alpha]_D^{21} - 6.0°$ (c=0.95, DMF); $Rf^1 = 0.25$.

Elemental analysis, for $C_{31}H_{51}O_6N_3S$: Calcd.: C, 62.71; H, 8.63; N, 7.08; S, 5.40; Found: C, 62.56; H, 8.82; N, 7.11; S, 5.43

EXAMPLE 22

Production of Z-Gly-Gly-OH

In 100 ml of water were dissolved under heating 15 g of Gly and 16.8 g of sodium hydrogencarbonate. The solution was cooled with ice. To the solution was added a solution of Z-Gly-ONB (prepared using 40 g of Z-Gly-OH) in 400 ml of THF under ice-cooling, followed by stirring for 40 hours. The resulting THF was distilled off and the solution was acidified with hydrochloric acid. Crystals were recovered by filtration and washed with water. Yield 44.4 g (87.3%); m.p. 169°–172° C.; $Rf^1 = 0.21$ Elemental analysis, for $C_{12}H_{14}O_5N_2$: Calcd.: C, 54.13; H, 5.30; N, 10.52; Found: C, 53.78; H, 5.10; N, 10.25

EXAMPLE 23

Production of Z-Tyr-Gly-Gly-OH 20 g of Z-Gly-Gly-OH in 500 ml of 80% aqueous acetic acid was subjected to catalytic reduction, and the solvent was distilled off. To the residue was added MeOH to cause crystallization. The crystals were recovered by filtration, and were then suspended in 75 ml of water. The suspension was dissolved with 5.92 g of sodium hydrogencarbonate. To the solution was added a solution of 31.8 g of Z-Tyr-ONB in 300 ml of THF under cooling with ice, followed by stirring for 15 hours. The THF was distilled off. To the residue were added 72 ml of 1 N-HCl. The mixture was subjected to extraction with 500 ml of n-butanol. The extract was washed with aqueous saturated solution of sodium chloride, followed by distilling off the solvent. To the residue was added diethyl ether, and the resulting crystals were recovered by filtration, followed by washing with AcOEt and then with aqueous acetonitrile. Yield 22.0 g (76.7%); m.p. 203°–206° C.; $[\alpha]_D^{21} - 19.8°$ (c=1.03, DMF); $Rf^1 = 0.10$.

Elemental analysis, for $C_{21}H_{23}O_7N_3$: Calcd.: C, 58.73; H, 5.40; N, 9.79; Found: C, 58.19; H, 5.47; N, 9.63

EXAMPLE 24

Production of Z-Tyr-Gly-Gly-Phe-Met(O)-OH

In 200 ml of TFA were dissolved 27.7 g of Boc-Phe-Met(O)-OH.DCHA. The solution was shaken at room temperature for 10 minutes, and the TFA was distilled off. To the residue was added diethyl ether, and the resulting precipitates were recovered by filtration and dried. The precipitates were dissolved in 400 ml of DMF, and the solution was neutralized with 13.7 ml of TEA under ice-cooling. A solution of Z-Tyr-Gly-Gly-ONB (prepared using 20.0 g of Z-Tyr-Gly-Gly-OH) in a small amount of DMF was added to the neutralized solution, followed by stirring at room temperature for 5 hours. The solvent was distilled off, and to the residue was added 5 ml of acetic acid and the mixture was subjected to extraction with 500 ml of n-butanol. The extract solution was washed with a saturated aqueous solution of sodium chloride, then the solvent was distilled off, and the residue was dissolved in 200 ml of MeOH. The solution was cooled with ice, followed by adding 150 ml of 1 N-NaOH, and the mixture was stirred for 1 hour, followed by neutralization with 150 ml of 1 N-HCl. Thus neutralized solution was subjected to extraction with n-BuOH. From the extract solution, the solvent was distilled off, and the residue was placed on a column (10×12 cm) of silica gel and the column was eluted with AcOEt: pyridine: acetic acid: water (60:16:5:8). Fractions of 2 to 4 l were collected and concentrated. To the concentrate was added diethyl ether. The resulting precipitates were recovered by filtration. Yield 16.9 g (50.1%); m.p. 87°–93° C.; $[\alpha]_D^{21} - 30.3°$ (c=0.90, DMF); $Rf^1 = 0.04$.

Elemental analysis, for $C_{35}H_{41}O_{10}N_5S \cdot H_2O$: Calcd.: C, 56.67; H, 5.84; N, 9.44; S, 4.32; Found: C, 56.41; H, 5.82; N, 9.25; S, 4.07

EXAMPLE 25

Production of H-Tyr-Gly-Gly-Phe-Met-OH

To 16.5 g of Z-Tyr-Gly-Gly-Phe-Met(O)-OH were added 12 ml of anisole and 100 ml of methanesulfonic acid, and the mixture was shaken at room temperature for 60 minutes, then cooled. To the mixture was added 1 l of diethyl ether to cause the precipitates to form. The diethyl ether layer was removed by decantation, and the residue was dissolved in 500 ml of water. The aqueous solution was allowed to pass through a column of Amberlite IRA-410 (acetic acid type). The thus treated solution was subjected to freeze-drying. The product was dissolved in 0.1 N acetic acid, and the solution was placed on a column (7×90 cm) of Sephadex LH-20 and eluted with 0.1 N acetic acid. Fractions of 2.2 to 2.8 l were collected and subjected to freeze-drying. Yield 10.7 g (78.9%); $[\alpha]_D^{21} + 25.1°$ (c=0.51, MeOH); $Rf^2 = 0.12$ (Avicel), $Rf^5 = 0.57$, $Rf^6 = 0.12$.

In 250 ml of 10% thioglycolic acid were dissolved 5.4 g weight out of the product thus obtained, and the solution was allowed to stand at 50° C. for 20 hours, then concentrated to about 40 ml, and the concentrate was placed on a column (7×90 cm) of Sephadex G-25. Elution was conducted with 20% acetic acid, and fractions of 2.56 to 3.44 l were collected, then subjected to freeze-drying. Yield 5.3 g (100%). The product was further dissolved in 30 ml of 10% acetic acid and placed on a column (7×90 cm) of Sephadex LH-20. Elution was conducted with 10% acetic acid, and fractions of 2.60 to 3.04 l were collected, then subjected to freeze-drying. Yield 4.90 g (93.2%). To 4.10 g taken out of the product that obtained were added 10 ml of water to cause crystallization. The crystals were recovered by filtration under cooling. Yield 3.45 g (84.1%); m.p. 198°–199° C.; $[\alpha]_D^{23} + 33.2°$ (c=0.53, water); $Rf^1 = 0.02$, $Rf^2 = 0.27$, $Rf^3 = 0.33$.

Elemental analysis, for $C_{27}H_{35}O_7N_5S \cdot H_2O$: Calcd.: C, 54.81; H, 6.30; N, 11.84; S, 5.42; Found: C, 55.42; H, 6.23; N, 11.80; S, 5.40

EXAMPLE 26

Production of Boc-Tyr-Gly-Gly-Phe-Met-OH

In 5 ml of 50% aqueous acetonitrile were dissolved 900 mg of H-Tyr-Gly-Gly-Phe-Met-OH. To the solution was added 0.52 ml of TEA. The mixture was cooled with ice, to which were added 720 mg of Boc-SDP, followed by stirring for 15 hours. The solvent was distilled off. The residue was dissolved in 10 ml of water, and the solution was washed with AcOEt. The aqueous layer was concentrated. To the residue were added 2 ml each of acetic acid and 80% EtOH. The mixtue was placed on a column (3×48 cm) of Sephadex LH-20. Elution was conducted with 80% EtOH, and fractions of 200 to 235 ml were collected and concentrated. The concentrate was dissolved in 30 ml of water and the solution was acidified with AcOH, which was then subjected to extraction with AcOEt. The extract was washed with water and dried over anhydrous sodium sulfate. The solvent was distilled off, and to the residue was added diethyl ether. The resulting powdery product was recovered by filtration and recrystallized from AcOEt. Yield 685 mg (68.7%); m.p. 159°–160° C. (decomp.); $[\alpha]_D^{24} - 16.8°$ (c=0.94, DMF); $Rf^1 = 0.21$, $Rf^2 = 0.68$, $Rf^3 = 0.41$.

Elemental analysis, for $C_{32}H_{43}O_9N_5S$: Calcd.: C, 57.04; H, 6.43; N, 10.40; S, 4.76; Found: C, 56.58; H, 6.47; N, 10.25; S, 4.76

EXAMPLE 27

Production of Boc-Tyr-Gly-Gly-Phe-Met-Lys(Boc)-Pro-OBu$^t$ 534 mg of Z-Lys(Boc)-Pro-OBu$^t$ were catalytically reduced in 50 ml of MeOH, then the solvent was distilled off, and the residue was dissolved in 15 ml of DMF. To the solution were added 676 mg of Tyr-Gly-Gly-Phe-Met-OH and 700 mg of HONB. The mixture was cooled at −5° C. and 400 mg of DCC were added, followed by stirring at −5° C. for 2 hours and at room temperature for 16 hours. The resulting precipitates of DCU were removed by filtration. To the residue was added water, and the resulting precipitates were recovered by filtration and reprecipitated from aqueous methanol. Yield 905 mg (85.7%); m.p. 209° C. (decomp.); $[\alpha]_D^{24} - 33.0°$ (c=0.50, DMF); $Rf^1 = 0.61$.

Elemental analysis, for $C_{52}H_{78}O_{13}N_8S$: Calcd.: C, 59.18; H, 7.45; N, 10.62; S, 3.04; Found: C, 59.04; H, 7.49; N, 10.42; S, 2.90

EXAMPLE 28

Production of Boc-Tyr-Gly-Gly-Phe-Met-Lys(Boc)-Pro-OH

In 8 ml of TFA were dissolved 800 mg of Boc-Tyr-Gly-Gly-Phe-Met-Lys(Boc)-Pro-OBu$^t$, and the solution, after shaking at room temperature for 60 minutes, was concentrated. To the concentrate was added diethyl ether, followed by recovering the resulting precipitates by filtration and drying. The precipitates were dissolved in 10 ml of DMF, and 0.34 ml of TEA and 440 mg of Boc-ONB were added to the solution followed by stirring at 0° C. for 2 hours and at room temperature for 10 hours. The solution was evaporated under reduced pressure to dryness. To the residue was added diethyl ether. The resulting precipitates were recovered by filtration and then placed on a column (2.5×115 cm) of Sephadex LH-20. Elution was conducted with MeOH and fractions of 195 to 225 ml were collected, then the solvent was evaporated to dryness under reduced pressure. To the concentrate was added diethyl ether, and the mixture was subjected to filtration to give the product. Yield 680 mg (90.9%); m.p. 151° C. (decomp.); $[\alpha]_D^{24} - 28.0°$ (c=0.52, DMF); $Rf^1 = 0.25$, $Rf^2 = 0.64$.

EXAMPLE 29

Production of Z-Leu-Leu-Lys(Boc)-His-Ile-Thr-Leu-Lys(Boc)-Asn-Glu(OBu$^t$)-Gln-OBu$^t$ A 3.0 g portion of Z-Leu-Lys(Boc)-Asn-Glu(OBu$^t$)-Gln-OBu$^t$ was catalytically reduced in 100 ml of DMF. After filtering out the catalyst, the filtrate was concentrated to about half the volume, to which 2.87 g of Z-Leu-Leu-Lys(Boc)-His-Ile-Thr-OH and 1.0 g of HONB were added. The reaction solution was cooled to −10° C., and 800 mg of DCC were added, followed by stirring at −10° C. for 2 hours, at 4° C. for 5 hours, and at room temperature for 12 hours. After filtering out insolubles, the solution was evaporated under reduced pressure to dryness, and diethyl ether was added. The resulting precipitate was recovered by filtration, and washed with acetonitrile and then with methanol. Yield 4.0 g (75.4%); m.p. >250° C.; $[\alpha]_D^{24} -19.2°$ (c=0.50, DMF); $Rf^6 = 0.65$.

Elemental analysis, for $C_{80}H_{143}O_{24}N_{17}$: Calcd.: C, 57.41; H, 8.01; N, 13.24; Found: C, 57.59; H, 8.31; N, 13.25

EXAMPLE 30

Production of Z-Leu-Ile-Thr-Leu-Leu-Lys(Boc)-His-Ile-Thr-Leu-Lys(Boc)-Asn-Glu(OBu$^t$)-Gln-OBu$^t$ A 3.6 g portion of Z-Leu-Leu-Lys(Boc)-His-Ile-Thr-Leu-Lys(Boc)-Asn-Glu(OBu$^t$)-Gln-OBu$^t$ was catalytically reduced in 50 ml of DMF. The catalyst was filtered out, and 1.1 g of Z-Leu-Ile-Thr-OH and 1.1 g of HONB were added to the filtrate. The mixture was cooled to −10° C., and 1.0 g of DCC was added, followed by stirring for 2 hours, at 5° C. for 6 hours and at room temperature for 8 hours. After filtering out insolubles, the filtrate was concentrated. To the residue was added diethyl ether. The resulting precipitate was recovered by filtration, and washed with acetonitrile and then with methanol. Yield 3.4 g (78.2%); m.p. >250° C.; $[\alpha]_D^{24} -17.0°$ (c=0.53, DMF); $Rf^6 = 0.67$.

Elemental analysis, for $C_{102}H_{172}O_{29}N_{20}$: Calcd.: C, 57.18; H, 8.09; N, 13.07; Found: C, 57.33; H, 7.97; N, 13.03

EXAMPLE 31

Production of Z-Tyr-Thr-Lys(Boc)-Gln-Ser-His-Lys(Boc)-Pro-Leu-Ile-Thr-Leu-Leu-Lys(Boc)-His-Ile-Thr-Leu-Lys(Boc)-Asn-Glu(OBu$^t$)-Gln-OBu$^t$ A 3.21 g portion of Z-Leu-Ile-Thr-Leu-Leu-Lys(Boc)-His-Ile-Thr-Leu-Lys(Boc)-Asn-Glu-Gln-OBu$^t$ was catalytically reduced in 50 ml of DMF, and after filtering out the catalyst, 2.12 g of Z-Tyr-Thr-Lys(Boc)-Gln-Ser-His-Lys(Boc)-Pro-OH and 0.36 g of HONB were added to the filtrate. The mixture was cooled at −10° C., and 0.412 g of DCC was added, followed by stirring at −10° C. for 4 hours, at 5° C. for 6 hours, and at room temperature for 8 hours. Insolubles were filtered out, and the filtrate was concentrated. To the concentrate was added AcOEt. The resulting precipitates were recovered by filtration and reprecipitated from aqueous methanol. Yield 5.02 g (99%); m.p. >250° C.; $[\alpha]_D^{24} -10.5°$ (c=0.55, DMF); $Rf^2 = 0.41$, $Rf^6 = 0.63$.

Elemental analysis, for $C_{156}H_{255}O_{48}N_{33}$: Calcd.: C, 55.75; H, 7.65; N, 13.75; Found: C, 56.08; H, 7.66; N, 13.78

EXAMPLE 32

Production of Boc-Tyr-Gly-Gly-Phe-Met-Lys(Boc)-Pro-Tyr-Thr-Lys(Boc)-Gln-Ser-His-Lys(Boc)-Pro-Leu-Ile-Thr-Leu-Leu-Lys(Boc)-His-Ile-Thr-Leu-Lys(Boc)-Asn-Glu(OBu$^t$)-Gln-OBu$^t$ In 40 ml of DMF were dissolved 672 mg of Z-Tyr-Thr-Lys(Boc)-Gln-Ser-His-Lys(Boc)-Pro-Leu-Ile-Thr-Leu-Leu-Lys(Boc)-His-Ile-Thr-Leu-Lys(Boc)-Asn-Glu(OBu$^t$)-Gln-OBu$^t$. The solution was subjected to catalytic reduction. After filtering out the catalyst, the filtrate was concentrated under reduced pressure to 20 ml, and there were then added 200 mg of Boc-Tyr-Gly-Gly-Phe-Met-Lys(Boc)-Pro-OH and 200 mg of HONB. The mixture was cooled to 0° C., and then 200 mg of DCC were added, followed by stirring for 12 hours. The DCU was filtered out, and the filtrate was evaporated under reduced pressure to dryness. The residue was dissolved in a small amount of MeOH. The solution was developed on a column (2.5×125 cm) of Sephadex LH-20 with MeOH. Eluted fractions of 140 to 185 ml were collected and evaporated under reduced pressure to dryness. To the residue was added AcOEt, and the resulting powder was recovered by filtration. Yield 710 mg (84.0%); m.p. >250° C.; $[\alpha]_D^{24} -13.7°$ (c=0.50 in DMF); $Rf^2 = 0.45$, $Rf^6 = 0.65$.

Elemental analysis, for $C_{196}H_{317}O_{59}N_{41}S$: Calcd.: C, 55.73; H, 7.57; N, 13.60; S, 0.76; Found: C, 56.19; H, 7.83; N, 13.55; S, 0.78

EXAMPLE 33

Production of H-Tyr-Gly-Gly-Phe-Met-Lys-Pro-Tyr-Thr-Lys-Gln-Ser-His-Lys-Pro-Leu-Ile-Thr-Leu-Leu-Lys-His-Ile-Thr-Leu-Lys-Asn-Glu-Gln-OH In 10 ml of a mixture of TFA-water (9:1) were dissolved 200 mg of the protected peptide as obtained in Example 32, and the solution was shaken at 20° C. for 60 minutes. The TFA was distilled off under reduced pressure. To the residue was added diethyl ether, and the resulting powder was recovered by filtration. The powder was dissolved in 10 ml of water and passed through a column (2.0×5 cm) of Amberlite CG-400 (acetic acid type). Freeze-drying of the thus treated solution resulted in 182 mg of powder. The powder was dissolved in 40 ml of water and the solution was poured into a column (2.4×27 cm) of carboxymethylcellulose. The column was washed with 100 ml of water followed by conducting gradient-elution with 500 ml of water and 500 ml of 0.3 M acetic acid-aqueous ammonia (pH 6.8). Elution fractions of 640 ml to 740 ml were collected and freeze-dried, resulting in 137 mg of powder. The powder was dissolved in a small amount of N-aqueous acetic acid. The solution was developed on a column (2.0×110 cm) of Sephadex LH-20 with N-aqueous acetic acid. Fractions of 72 to 99 ml were collected and freeze-dried, thus resulting in the desired peptide. Yield 109 mg; $[\alpha]_D^{24} -80.0°$ (c=0.13 in N-acetic acid); $Rf^4 = 0.57$ (cellulose), $Rf^5 = 0.64$ (cellulose); amino acid analysis: Lys 5.08; His 1.96, Asp 1.00, Thr 3.09, Ser 0.92, Glu 3.09, Pro 2.01, Gly 2.10, Met 0.94, Ile 1.98, Leu 4.02, Tyr 1.98, Phe 1.00 (allo-Thr content <0.3%), (recovery rate of 88%).

EXAMPLE 34

Preparation of injections:

Compound I (10 mg) and mannitol (100 mg) were dissolved in sterilized distilled water (10 ml). Ampoules were filled, each with 1 ml of the foregoing solution, and were then lyophilized. The powder thus obtained may be used as an injection by dissolving it in physiological saline solution (1 ml).

Variations can of course be made without departing from the spirit of our invention. For instance, although Example 32 relates to the production of a compound of formula (II) by utilizing the compounds of Example 28 and Example 31 as the specific "building blocks", other (different) building blocks may also be utilized. See, e.g., the specification at page 4, line 27-page 6, line 26.

What we claims is:

1. The compound of the formula:

H-Tyr-Gly-Gly-Phe-Met-Lys-Pro-Tyr-Thr-Lys-Gln-Ser-His-Lys-Pro-Leu-Ile-Thr-Leu-Leu-Lys-His-Ile-Thr-Leu-Lys-Asn-Glu-Gln-OH, or a pharmaceutically acceptable salt thereof.

2. An analgesic composition which comprises an analgesically effective amount of a compound as defined in claim 1, together with a pharmaceutically acceptable carrier.

* * * * *